(12) United States Patent
Mensink et al.

(10) Patent No.: US 12,096,987 B2
(45) Date of Patent: Sep. 24, 2024

(54) METHOD AND ASSEMBLY FOR SPATIAL MAPPING OF A MODEL, SUCH AS A HOLOGRAPHIC MODEL, OF A SURGICAL TOOL AND/OR ANATOMICAL STRUCTURE ONTO A SPATIAL POSITION OF THE SURGICAL TOOL RESPECTIVELY ANATOMICAL STRUCTURE, AS WELL AS A SURGICAL TOOL

(71) Applicant: AugmedIT B.V., Naarden (NL)

(72) Inventors: Thomas Jacobus Andreas Mensink, Naarden (NL); Theodorus Petrus Cornelis van Doormaal, Naarden (NL)

(73) Assignee: AugmedIT B.V., Naarden (NL)

(*) Notice: Subject to any disclaimer, the term of this patent is extended or adjusted under 35 U.S.C. 154(b) by 423 days.

(21) Appl. No.: 17/421,077

(22) PCT Filed: Jan. 10, 2020

(86) PCT No.: PCT/NL2020/050015
§ 371 (c)(1),
(2) Date: Jul. 7, 2021

(87) PCT Pub. No.: WO2020/145826
PCT Pub. Date: Jul. 16, 2020

(65) Prior Publication Data
US 2022/0110684 A1    Apr. 14, 2022

(30) Foreign Application Priority Data
Jan. 10, 2019 (NL) ..................................... 2022371

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/39* (2016.02);
(Continued)

(58) Field of Classification Search
CPC ......................... A61B 34/10; A61B 2034/102
See application file for complete search history.

(56) References Cited

U.S. PATENT DOCUMENTS

2016/0249985 A1    9/2016  Haimerl et al.
2017/0056115 A1    3/2017  Corndorf et al.
(Continued)

*Primary Examiner* — Samantha (Yuehan) Wang
(74) *Attorney, Agent, or Firm* — Hoffmann & Baron, LLP

(57) ABSTRACT

A method for the spatial mapping of a model of a surgical tool onto a spatial position of the surgical tool includes a) providing a surgical tool having a working part and a marker in the form of a visual image on a surface; b) providing a tool model of the surgical tool; c) providing a viewing device configured to be carried by a user and including a camera configured to capture a view and to generate camera data representative of the view; d) creating a spatial model of a space viewed by the camera; e) bringing the surgical tool within the space viewed by the camera; f) identifying a representation of the marker in the camera data; g) determining a position and rotation of the representation of the marker with respect to the spatial model, and h) creating a spatial mapping of the tool model in the spatial model.

18 Claims, 6 Drawing Sheets

(51) Int. Cl.
*A61B 90/00* (2016.01)
*A61B 90/50* (2016.01)

(52) U.S. Cl.
CPC ... *A61B 2034/102* (2016.02); *A61B 2034/105* (2016.02); *A61B 2034/2057* (2016.02); *A61B 2034/2065* (2016.02); *A61B 2034/2068* (2016.02); *A61B 2090/3937* (2016.02); *A61B 2090/3983* (2016.02); *A61B 2090/502* (2016.02)

(56) References Cited

U.S. PATENT DOCUMENTS

| | | | |
|---|---|---|---|
| 2018/0116732 A1 | 5/2018 | Lin et al. | |
| 2018/0168740 A1* | 6/2018 | Ryan | A61B 90/36 |
| 2020/0214772 A1* | 7/2020 | Srimohanarajah | G16H 30/40 |

* cited by examiner

ID AND ASSEMBLY FOR SPATIAL
MAPPING OF A MODEL, SUCH AS A
HOLOGRAPHIC MODEL, OF A SURGICAL
TOOL AND/OR ANATOMICAL STRUCTURE
ONTO A SPATIAL POSITION OF THE
SURGICAL TOOL RESPECTIVELY
ANATOMICAL STRUCTURE, AS WELL AS A
SURGICAL TOOL

CROSS-REFERENCE TO RELATED
APPLICATIONS:

This application is the National Stage of International Application No. PCT/NL2020/050015, filed Jan. 10, 2020, which claims the benefit of Netherlands Application No. 2022371, filed Jan. 10, 2019, the contents of which is incorporated by reference herein.

TECHNICAL FIELD

The present invention relates to a method and assembly for the spatial mapping of a digital model—such as a 3D-model also known (correctly or not) to the public as a hologram—of a surgical tool and/or anatomical structure onto a spatial position of the surgical tool respectively anatomical structure, and to a surgical tool suitable for use in the method and assembly.

BACKGROUND OF THE INVENTION AND
PROBLEMS OF THE PRIOR ART

The tracking of medical physical tools and patient fixation frames is currently used in the medical world to give detailed feedback to a surgeon during an operation. The combination of the pose (i.e. position and rotation) of the tools and a patient fixation frame gives valuable information concerning the location of the working part of the tools with respect to the patient. This is, for example, useful in brain surgery, where precision is highly important.

Current tracking methods work with tracking markers placed on the tools and fixation frames, where the markers are three dimensional structures such as small spheres e.g. recognizable by infrared cameras, or contain magnetic markers. An external system comprising A detection system detects these markers and is thus able to determine the pose of the connected objects in 6-dimensional space (3 position coordinates and 3 rotation coordinates). This detection system either has two stereo IR cameras or magnetic sensors which are arranged at predetermined points fixed and unmoveable with respect to the real world. Both types of systems are capable of getting the position of multiple tracking markers at the same time. A medical two or three dimensional model of the patient, e.g. derived from acquired MRI, CT, PET or sound scans, are then positioned in the same coordinate system as the one obtained with the external system. In order to do this, there will be some kind of match between the real world and the images or models.

There are some problems with this current way of working. Most importantly, the systems with the external cameras are very expensive with costs of more than €400.000,-. This restricts the number of devices that can be obtained by a hospital, if it can be obtained at all in certain countries, and thus considerably restricts the application of the device.

Additionally, the systems are normally displaying the resulting two or three dimensional scenes on a flat screen, somewhere above the patient. This is not only unnatural, but also results in neck problems of the medical personal having to look up instead of down at the patients. Due to being unnatural, it negatively affects the eye-hand-coordination of the surgeon.

Further, the systems require an external heavy and relatively large camera system, which does not allow a quick and easy setup in other environments than a well-controlled operation room.

Lastly, the system only works when a real patient is present, and can thus not be used for training or preparation purposes in a fully virtual environment.

The present invention provides an improved method of the spatial mapping of the tool which can solve the above-mentioned problems.

SUMMARY OF THE INVENTION

The present invention discloses a method for the spatial mapping of a digital model of a surgical tool onto a spatial position of the surgical tool. This spatial mapping is a determination, such as a digital determination by a processor unit, of the position and rotation of the surgical tool with respect to reference points in space, preferably with respect to the patient. This spatial mapping according to the invention can be used to determine the exact location of specific parts of a tool with respect to a patient, which may be useful when the tools are used for internal surgery and cannot be fully seen by the user. The spatial mapping according to the invention may also be used for educational purposes in educating doctors or for training doctors. In training and education a corpse, a physical model or an imaginary model, like a hologram, may be used. In the continuation of training/education, the spatial mapping according to the invention may also be used in informing patients about an illness or surgical procedure to be performed. Further, the measured location of the tool can be used to locate multiple markers on the patients real head or body, which are then used to calculate the pose (i.e. position and rotation) of the patient and thus be able to accurately superimpose a 3D model of anatomical structures over the patient's body.

The method according to the first aspect of the invention is a method for the spatial mapping of a model of a surgical tool onto a spatial position of the surgical tool, which method comprises the following steps:

Providing a surgical tool having a working part and a marker in the form of a visual image on a surface, such as a bitmap image, the marker being arranged at a pre-determined marker location fixed relative to the working part of the surgical tool. This fixed location is important, because the spatial mapping is based on the marker. The desired location of the working part can be unambiguously determined once the position and rotation of the marker is known. A visual image is understood to be an image which is visible for a regular camera capturing views also visible for the human eye. In general, one may say that a visual image is an image visible for the human eye.

Providing a tool model of the surgical tool, the tool model comprises at least the working part of the surgical tool and its location relative to the marker. This tool model may be a digital model which may for example i) be used to visualize the location of the working part, when the user cannot directly see the working part of the surgical tool itself, for example when it is submerged in the patient, ii) be used to generate a warning signal when a wrong manoeuvre is done or when a specific region is approached, iii) be used for archiving purposes in order to review a surgical procedure at a later stage, iv) be used to measure multiple points on the patients head or body, which are used to calculate the exact position of 3D anatomical models which can be superimposed on the patient, etcetera. In general, it is very useful if the tool model is very similar to the actual tool. According to an embodiment, the tool model may for example also be a hologram or in case of a digital model, the digital model may be transformed into a hologram.

Providing a viewing device configured to be carried by a user and comprising:
  a camera configured for:
    capturing a view from a user's point who is wearing the viewing device, and
    capturing the visual image when the image is within the view,
    generating camera data representative of the view captured by the camera. According to an embodiment, the camera may, for example, be one or more cameras mounted on goggles or on another headwear, like an helmet.

Creating, on the basis of the camera data, a spatial model of a space viewed by the camera. This may, for example, be done through techniques known in augmented reality, for example applied in the HoloLens® of Microsoft®. A spatial model may for example be obtained by making a mapping of recognizable points, such as corners of rooms or contrast rich objects, in space which are tracked over time.

Bringing the surgical tool within the space viewed by the camera so that the camera captures the visual image.

Identifying in the camera data a representation of the marker. This representation is that part of the camera data which is associated with the marker and its visual image (this said part of the camera data will further also be called 'image data'). Having identified the camera data associated to the marker and its visual image, further information needed can be obtained in a next step.

Determining, on the basis of the camera data and the spatial model, a position and rotation of the marker with respect to the spatial model. In other words, on the basis of the camera data, the position and rotation of the representation of the marker in the captured camera data is determined with respect to the spatial model. The visual image is configured to provide image data captured by the camera, which image data are dependent from the position and rotation of the visual image with respect to the camera. In other words, the content of these image data will depend from the position of the marker/visual image with respect to the camera as well as from the rotation of the marker/visual image with respect to the camera. This allows determination of the position and rotation of the marker with respect to the spatial model.

Creating a spatial mapping of the tool model in the spatial model, the creation of the spatial mapping being based on the tool model and the determined position and rotation of the marker. The spatial mapping of the tool gives information regarding the location of the working part of the surgical tool with respect to its surroundings.

In a further embodiment of the first aspect, the method according to the invention may further comprise the steps of: moving the surgical tool to a multiple of (calibration) positions and/or rotations within the space viewed by the camera, such as at least 4, preferably at least 8, positions and/or rotations within the space viewed by the camera,
  capturing a first set of camera data at each position and/or rotation,
  creating, for each first set of camera data, a said spatial mapping of the tool model in the spatial model,
  (optionally, visually correcting the position of the tooltip of the virtual tool and as such creating a second set of camera data,) and
  obtaining a corrected spatial mapping of the tool model in the spatial model by processing the created first (and optionally second) sets of spatial mappings with a calibration algorithm, such as an interpolation or artificial intelligence script.

Inaccuracies caused by the camera-chip, for example due to limited resolution or bad pixels of the camera-chip, in the determination of the position and rotation of the marker, or inaccuracies of other origin may thus be reduced or eliminated. Such a calibration thus allows increasing the accuracy of the tool model in relation to the real world. The multiple of positions and rotations may be positions and rotations which are predetermined, for example, relative to the real world or relative to the space viewed by the camera. But these multiple of positions and rotations may also be random or not predetermined, which makes the calibration easier for the user to be carried out. Also a combination of predefined positions and/or rotations and random positions and/or rotations may be used.

In a further embodiment of the first aspect, the method according to the invention may further comprise the steps of:
  generating, on the basis of:
    the spatial mapping of the tool model in the spatial model or
    the corrected spatial mapping of the tool model in the spatial model, a visual tool image representing the surgical tool, and
  superimposing the visual tool image in the view onto the surgical tool and/or onto a predetermined location shifted relative to the surgical tool.

A visual tool image indicates an image which is visible for the user carrying the viewing device. This may for example be a hologram. The visual tool image may be about identical to the (real) surgical tool with or without the marker. By superimposing the visual tool image onto the surgical tool, the (real) surgical tool becomes so to say hidden behind the visual tool image. In this respect it is noted that leaving away the marker from the visual tool, provides that the marker on the real visible tool is better visible for the camera. Generating a visual tool image representing the surgical tool and superimposing the visual tool image onto the surgical tool, enables use in augmented reality devices.

By superimposing the visual tool image onto a predetermined location shifted relative to the surgical tool, a visual tool image may be visible for the user carrying the viewing device in isolation from the (real) working area of the surgical tool.

In relation to superimposing the visual tool image onto the surgical tool, it is to be noted that this may be realised with technology know from the prior art. It may for example be realised by means of a projector projecting a hologram in front of the user in the space viewed by the eyes of the user. According to another example, it may also be realised by means of a projector projecting the image directly into the eye of the user, instead of projecting it somewhere in front of the user. Also this is as such known technology.

In a further embodiment of the method according to the invention, the visual tool image may be projected into the view whilst the surgical tool is within the view of the user—such as projected forwardly in the space before the eyes of the user or backwardly directly into the eyes of the user—and partly visible for the camera and/or user. This supports a surgeon in precisely positioning or manoeuvring the tool, for example, inside the body of a patient, or with respect to other tools or other images shown by the augmented reality device.

According to a second aspect of the invention, which may be separate of the first aspect of the invention but may also be a further embodiment of the first aspect, the method according to the invention may further comprise the steps of:

Providing, on the basis of a scan of an object, a visual 3-dimensional image of an object, the object having a multiple of reference points and the visual 3-dimensional image including per reference point an image point representative of the position of the associated reference point in the visual 3-dimensional image. The object may be a patient, part of a patient's body such as its head, brain, tumor, or a corpse or part of a corpse's body. The scan may for example be an MRI-scan, a CT-scan, a PET-scan, an X-ray-scan, a sound scan, another type of scan or a combination of scans. These scans are in general basically 2D scans. Creating a 3-dimensional image, such as a surface or volume model, on the basis of a multiple of these 2D scans is as such known technology.

Touching with the pointed part the multiple of reference points on the object within the space viewed by the camera.

Capturing, at each touching of a reference point, a second set of camera data.

Determining for each reference point, on the basis of the tool model, the spatial model, and the associated second set of camera data, a spatial position representative of the position of the respective reference point within the spatial model. This can be for example done with existing point cloud matching techniques.

Projecting the visual 3-dimensional image into the view.

This allows a 3D-image of, for example, the brains of a patient to be projected into the view so that the surgeon is able to see it.

In a further embodiment of the second aspect, the visual 3-dimensional image may, in the step of projecting, be projected into the view by superimposing each image point onto its associated spatial position. This allows a 3D-image of, for example, the brains of a patient to be projected precisely onto the head of the patient. Such a 3D-image allows the surgeon to see precisely what will come on his way when entering into the body of the patient. In case this is combined with superimposing the visual tool image onto the surgical tool, the surgeon may see precisely where, inside the body of the patient, the surgical tool is and what he is doing.

In another further embodiment of the second aspect, the visual 3-dimensional image may, in the step of projecting, be projected into the view by superimposing each image point onto a predetermined location in the view, which predetermined location is shifted relative to the associated spatial position. This, for example, allows the surgeon to not only see the 3D-image projected precisely onto the head of the patient, but to see also an isolated view of the brains of a patient. In case this is combined with superimposing the visual tool image onto a correspondingly shifted location, the surgeon may see precisely, both on the head of the patient and in isolated view, where, inside the body of the patient, the surgical tool is and what he is doing. The predetermined locations of each to be superimposed image point may be shifted relative to the associated spatial position, such that this projection yields a 3-dimensional image that is similar in size, larger in size, or smaller in size compared with a projection onto the associated spatial positions and/or similar in rotation, or rotated relative to a projection onto the associated spatial positions. The latter may allow the surgeon to see precisely what is happening in the same perspective of the head of the patient, and/or have a view showing another, rotated perspective of what will come his way when entering the body, and/or where inside the body of the patient, the surgical tool is and what he is doing.

It is to be noted that "projecting the visual 3-dimensional image into the view by superimposing each image point onto a predetermined location in the view, which predetermined location is shifted relative to the associated spatial position", may also be without "projecting the visual 3-dimensional image into the view by superimposing each image point onto its associated spatial position". This allows a 3D-image of, for example, the brains of a patient to be projected shifted relative to the head of the patient. Such a 3D-image allows the surgeon to see precisely what will come on his way when entering into the body of the patient, in isolation from the view of the patient and without obscuring the view of the patient at the location where the surgeon is treating the body of the patient. In case this is combined with superimposing the visual tool image onto the surgical tool, the surgeon may see precisely where, inside the body of the patient, the surgical tool is and what he is doing. The predetermined locations of each to be superimposed image point may be shifted relative to the associated spatial position, such that this projection yields a 3-dimensional image that is similar in size, larger in size, or smaller in size compared to a projection onto the associated spatial positions and/or similar in rotation, or rotated relative to a projection onto the associated spatial positions. The latter may allow the surgeon to see precisely what is happening in the same perspective as that of the head of the patient, and/or have a view showing another, rotated perspective of what will come his way when entering the body, and/or where inside the body of the patient, the surgical tool is and what he is doing.

In a further embodiment of the method according to the second aspect of the invention, the reference points may comprise mark points provided on the object. For example, small marks may be placed on the head of a patient during a scan, by which they are incorporated in the scan model. By precise touching of these marks with the pointing element, the scan can then be shown in the correct location in augmented reality.

In a further embodiment of the method according to the second aspect of the invention, the reference points may comprise characteristic points of a contour of the object. The characteristic points may, for example, comprise predefined characteristic points. It is for example possible to use the surgical tool for drawing lines forming a 3D-surface, in which case the characteristic points may be points on these lines or these lines constitute a sequences of characteristic points.

In a further embodiment of the second aspect, the spatial positions added into the spatial model may be used as reference points for adding into the spatial model one or more additional models which comprise reference points, such as models of body parts which comprise reference points on the skin.

In a further embodiment of the method according to the second aspect of the invention, the method may comprise a step of providing a marker frame to be attached to the object, which marker frame comprises a said reference point and is provided with a set of at least two frame markings, the frame markings of the set being arranged at mutually spaced, fixed positions on the frame and the said reference point being arranged at a predetermined reference point position fixed relative to the frame markings. This allows for determining the position of the reference point in a highly accurate fashion, as the mutually spaced, fixed positions on the frame are known parameters. This may be of importance for (small) corrections required for the position of the reference point due to (minor) movements of the object, for example the head of a patient. In a further embodiment the set of frame markings may comprise three object markings, which allows for accurate corrections for both translational movements and/or rotations of the object in the view. Each frame marking may, according to a another further embodiment, be in the form of a visual image on a surface, such as a bitmap image.

In a further embodiment of the method according to the first aspect of the invention, possibly in combination with the second aspect of the invention, the visual marker may comprise information about the shape and size of the surgical tool, and wherein, in the step of providing a tool model, the tool model is created on the basis of this information. This enables using different surgical tools in a surgical procedure, without it being required that the tool models are to be known in advance. They are so to say loaded into the system by showing them to the camera. In a further embodiment of the method according to the invention, the tool image may be generated on the basis of said information.

In a further embodiment of the method according to the first aspect of the invention, possibly in combination with the second aspect of the invention, the visual image may be no larger than 50 cm$^2$, such as no larger than 40 cm$^2$, and preferably not smaller than 36 cm$^2$, in order to be accurate enough. It may for example be square about 6×6 cm. It should also not be much larger in order to be practical enough.

In a further embodiment of the method according to the first aspect of the invention, possibly in combination with the second aspect of the invention, the marker of the surgical tool may comprise a set of at least two tool markings, the tool markings of the set being arranged at mutually spaced, fixed positions on the surgical tool. This allows for determining the position of the tool in a highly accurate fashion, as the mutually spaced, fixed positions on the frame are known parameters. In a further embodiment, the set of tool markings may comprise three tool markings, which allows for accurately determined positions for both translational movements and/or rotations of the tool, even for very small movements and/or rotations. Each tool marking may, according to a another further embodiment, be in the form of a visual image on a surface, such as a bitmap image.

According to a third aspect, the invention provides an assembly for creating a spatial mapping of a digital model of a surgical tool on a spatial position of a surgical tool, comprising:
- a surgical tool having a working part and a marker in the form of a visual image on a surface, such as a bitmap image, the marker being arranged at a pre-determined marker location fixed relative to the working part of the surgical tool,
- a data carrier, configured to carry at least data of a digital tool model of the surgical tool, the tool model comprising at least the working part of the surgical tool and its location relative to the marker, and
- a viewing device configured to be carried by a user and comprising:
    - a camera configured to:
        - capture a view from a user's point who is wearing the viewing device,
        - capture the image when the image is within the view, and
        - generate camera data representative of the view captured by the camera,
    - a processor unit.

According to a further embodiment of the third aspect, the processor unit may be configured to carry out the method according to one of the invention.

According to another further embodiment of the third aspect, the processor unit may be configured to:
- receive the camera data,
- create, on the basis of the camera data received, a spatial model of a space viewed by the camera,
- identify a representation of the marker in the camera data,
- determine, on the basis of the camera data and the spatial model, a position and rotation of the representation of the marker with respect to the spatial model, and
- create a spatial mapping of the tool model in the spatial model, the creation of the spatial mapping being based on the tool model and the determined position and rotation of the marker.

According to another further embodiment of the third aspect, the processor unit may be further configured to:
- receive a multiple of first sets of camera data captured by the camera, such as at least 4 first sets, preferably at least 8 first sets,
- create, for each first set of camera data, a said spatial mapping of the tool model in the spatial model, and
- obtain a corrected spatial mapping of the tool model in the spatial model by processing the created spatial mappings with a calibration algorithm, such as an interpolation or artificial intelligence script.

According to a further embodiment of the third aspect, the viewing device may further comprise a projector configured to project a projection superimposed over the view.

According to a further embodiment of the third aspect, the processor unit and projector may be configured to:
- generate, on the basis of:
    - the spatial mapping of the tool model in the spatial model or
    - the corrected spatial mapping of the tool model in the spatial model, a visual tool image representing the surgical tool, and
- superimpose, by means of the projector, the visual tool image in the view onto the surgical tool and/or onto a predetermined location shifted relative to the surgical tool.

According to a further embodiment of the third aspect, the processor unit and projector may further be configured to project the visual tool image into the view whilst the surgical tool is within the view and partly visible for the camera and/or user.

According to a fourth aspect of the invention, which may also be to a further embodiment of the third aspect of the invention, in which the working part defines a pointed part, the processor unit and projector may further be configured to:
- receive a visual 3-dimensional image of an object, wherein the 3-dimensional image has been obtained on the basis of a scan of the object, and wherein the object has a multiple of reference points and the visual 3-dimensional image includes per reference point an image point representative of the position of the associated reference point in the visual 3-dimensional image, receive, per reference point, a second set of camera data captured by the camera when said reference point is touched by the pointed part, determine for each reference point, on the basis of the tool model, the spatial model, and the associated second set of camera data, a spatial position representative of the position of the respective reference point within the spatial model; and project the visual 3-dimensional image into the view.

The processor unit and projector may further be configured to project the visual 3-dimensional image into the view by superimposing each image point onto its associated spatial position and/or by superimposing each image point onto a predetermined location in the view shifted relative to the associated spatial position.

According to a further embodiment of the fourth aspect, the assembly may further comprise a marker frame, which marker frame comprises a said reference point and is provided with a set of at least two frame markings, the frame markings of the set being arranged at mutually spaced, fixed positions on the frame and the said reference point being arranged at a predetermined reference point position fixed relative to the frame markings. In a further embodiment of the second aspect, the set of frame markings may comprise three frame markings.

According to a further embodiment of the third aspect, the data carrier may be comprised in the visual marker, and the processor unit may be configured to create the tool model and/or tool image on the basis of the data of the tool model as comprised in the visual marker.

According to a further embodiment of the third aspect, the visual image may be no larger than 50 cm$^2$, such as no larger than 40 cm$^2$, preferably not smaller than 36. cm$^2$.

According to a further embodiment of the third aspect, the marker of the surgical tool may comprise a set of at least two tool markings, the tool markings of the set being arranged at mutually spaced, fixed positions on the surgical tool. In a further embodiment of the second aspect, the set of tool markings may comprise three tool markings.

According to a fifth aspect, the invention provides a surgical tool having a working part, which surgical tool further has a marker in the form of a visual image on a surface, such as a bitmap image, the marker being immovable relative to the working part and at a fixed location relative to the working part.

According to a further embodiment of the fifth aspect, the marker on the surgical tool comprises information about the shape and size of the surgical tool, from which information the digital tool model can be created.

According to a further embodiment of the fifth aspect, the information comprised in the marker is comprised in the visual image, wherein the image is a data carrying image, such as a bitmap image.

According to a further embodiment of the fifth aspect, the marker of the surgical tool may comprise a set of at least two tool markings, the tool markings of the set being arranged at mutually spaced, fixed positions on the surgical tool. In a further embodiment of the third aspect, the set of tool markings may comprise three tool markings.

According to a further embodiment of the fifth aspect, the marker image is no larger than 50 cm$^2$, such as no larger than 40 cm$^2$, preferably not smaller than 36 cm$^2$.

BRIEF DESCRIPTION OF THE DRAWINGS

The invention will further be elucidated with reference to the drawings, in which:

FIG. 6 shows how a tool with a pointing element can be used to project a visual 3-dimensional image of an object onto the object.

DETAILED DESCRIPTION OF THE INVENTION

Figure 1:
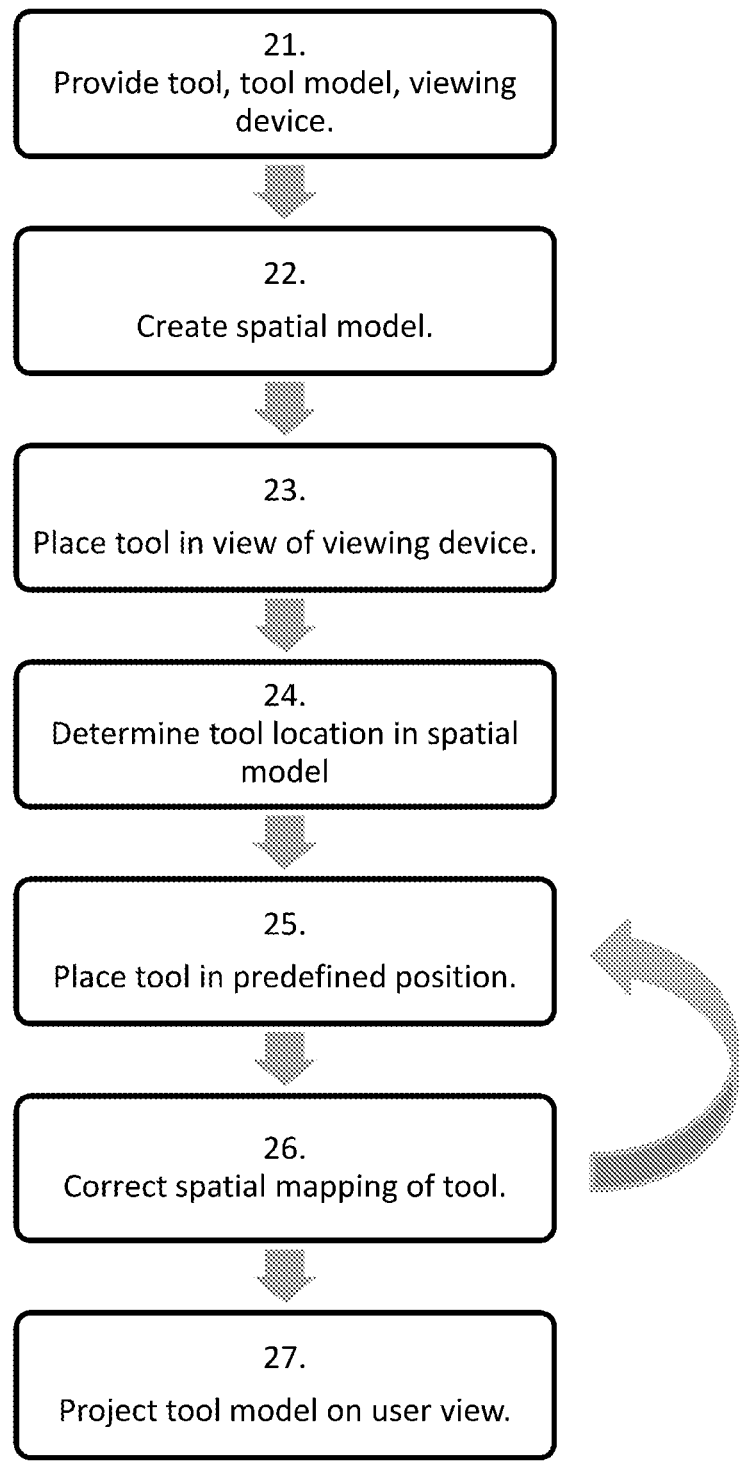
FIG. 1 shows a schematic overview of the method.

FIG. 1 is a step by step description of one embodiment of a method according to the invention.

Block 21 shows the first step: 'Provide tool, tool model, viewing device'. The required equipment for the method is provided to the user. With additional reference to FIGS. 2-6 for the reference numbers, a surgical tool 1, with a working part 2 and a marker 3, is provided. A tool model 4 of said surgical tool 3 is also provided, wherein the location of the working part 12 with respect to the marker 13 is the same as for the actual surgical tool 1. Additionally, a viewing device 5 configured to be carried by the user is provided. This viewing device 5 comprises at least a camera 6, but may also comprise a processor 7 and/or an augmented reality device 8.

Block 22, 'create spatial model', encompasses the second step. In this step, the data coming from the camera 6 on the viewing device 5 is transferred into a spatial model 20 of the space viewed by the camera 6. This three dimensional model is similar to the space in front of the camera 6. Significant unmoving shapes in this space, such as walls, tables or cabinets, are recognized by software and may be used as reference points for other items in the space. When the user moves, and thus the camera 6 moves, the relative location of the camera 6 to these items is tracked, and the spatial model 20 is updated where necessary.

When the spatial model 20 is created, the next step is to place the surgical tool 1 within the view of the viewing device 5 (block 23). By placing the tool within the view of the camera 6, it becomes part of the spatial model 20 and its movement is tracked, as happens for any object placed within the view of the camera 6. In block 24 ('Determine tool location in spatial model'), the marker 3 of the surgical tool 1 is recognized in the camera data, and the location of the surgical tool 1 in the spatial model 20 is determined. Because the location of the working part 2 of the surgical tool 1 with respect to the marker 3 is known from the tool model 4, the location of the working part 3 in the spatial model 20 is also known.

The further steps are optional additions, which are not required to have a working method but may improve the experience of the user. Block 25 ('Place tool in predefined position') and 26 ('Correct spatial mapping of tool') are used to improve the determined location of the tool in the spatial model, and are repeatable steps for enhancement of the improvements. The surgical tool 1 is first placed in a predefined position, with respect to the space in front of the camera 6. This may be a position which may be recognized in the spatial model 20. For example, the surgical tool may be placed exactly on the corner of a table, against a wall, or against a device which is used to restrain the patient. In these positions, the location of the working part 3 of the tool 1 is known by the script. As such, it can correct the mapping it receives through measuring the location of the marker 2, to fit with the known location of the working part. By repeating this correction, the mapping of the surgical tool becomes additionally accurate.

Block 27, 'Project tool model on user view', can be performed in case the viewing device comprises an augmented reality device 8. The tool model 4 is then projected on the mapped location of the surgical tool 1, over the users view. This may for example be done using augmented reality goggles, or through hologram-projections in space. It can show the entire tool model 4 to the user, even when part of the actual surgical tool 1 is blocked from view, for example because it is submerged in a patient. This is particularly useful for surgical actions which require precision in a spot which cannot be seen by the natural eye.

Figure 2:
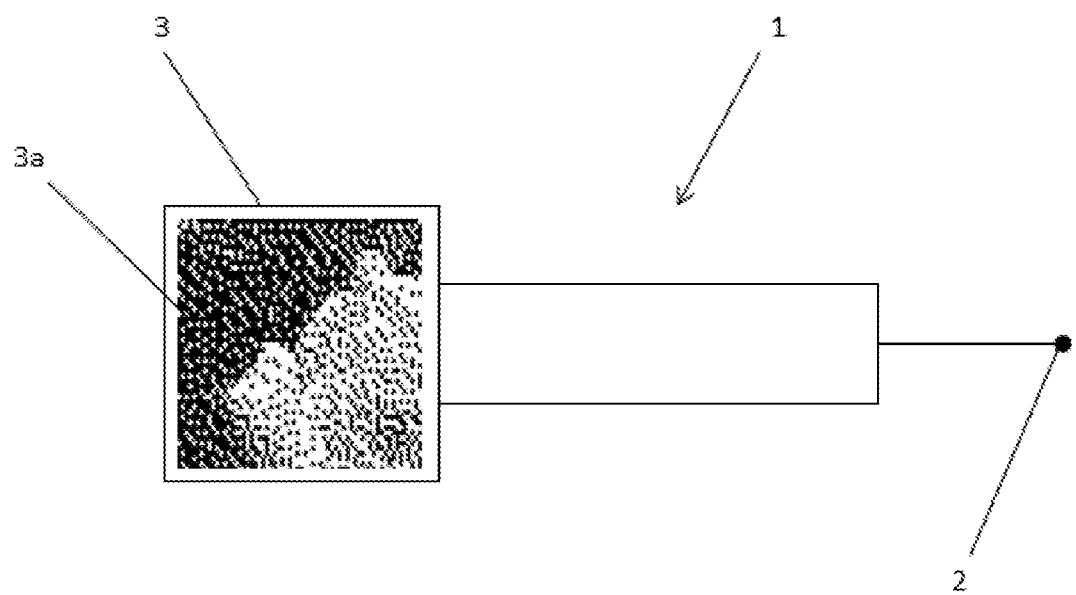
FIG. 2 shows a simplified model of the surgical tool, including a marker, visual image and a working part.

FIG. 2 shows highly schematic a surgical tool 1 which may be used in the method according to the invention. It comprises a working part 2, which may be a pointing element, a needle, tweezers, a knife-blade or any other part used in surgery. This working part 2 is placed at a fixed location with respect to a marker 3. The marker 3 may be any surface on which a visual image 3a can be placed. This visual image 3a can be any type of image, but it must be sufficiently distinct to be recognizable by software designed for that purpose. It may be a data carrying image such as a bitmap image, which carries sufficient data to make a digital model of the surgical tool, or which may allow the associated software to know which known tool model is associated with the tool.

Figure 3:
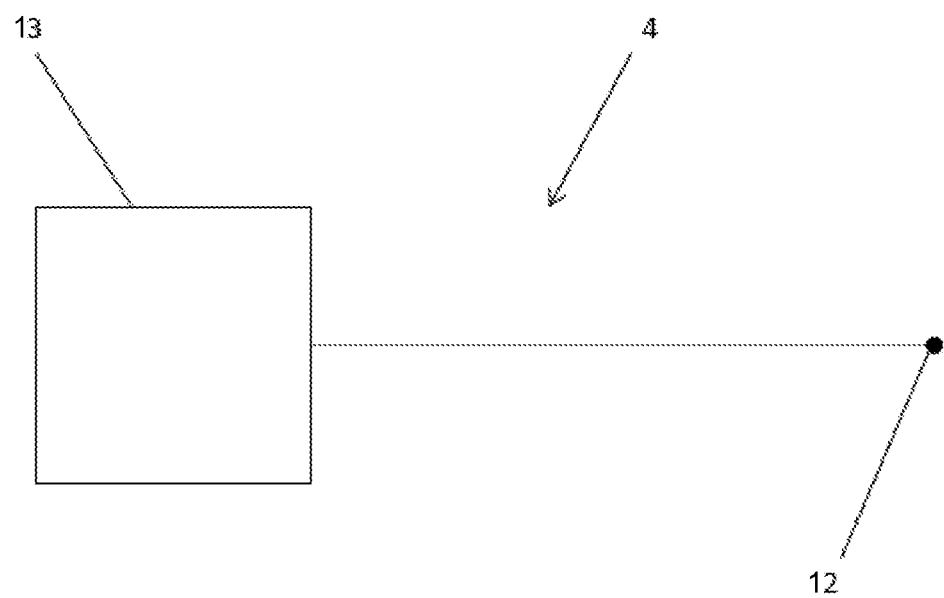
FIG. 3 shows the tool model associated to the surgical tool shown in FIG. 2, including the working part of the tool model and its location with respect to the marker of the tool model.

FIG. 3 shows the tool model 4 associated with the surgical tool 1 shown in FIG. 2. It comprises at least the location of the working part 12 associated to the working part 2 of the surgical tool 1 and the location of the marker 13 associated to the marker 3 of the surgical tool 1. The model may also show some of the design of the surgical tool 1, but this is not necessary for the method of the invention.

Figure 4:
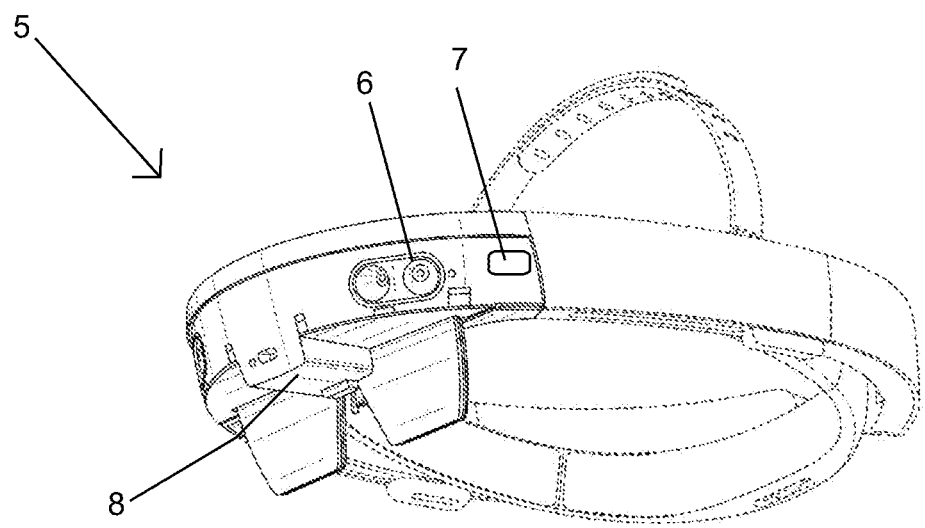
FIG. 4 shows an example of a viewing device.

FIG. 4 shows an example of a viewing device 5, where the viewing device 5 can be worn as glasses by the user. Many other configurations may be possible. The viewing device has at least one camera 6. It is useful to have the camera 6 close to the eyes of the user, so that the view of the camera is similar to the view of the user. The closer the camera is to the eyes of the user, the less there is required a correction of the view captured by the camera in order to match it to the view of the eyes of the user. This allows the user to instinctively place the surgical tool 1 within the view of the camera 6 by placing it within his/her own view.

The viewing device 5 may also comprise a processor 7. This processor may be used as a storage device for data, such as the tool model 4, and may also be used for the creation of the spatial model, identification of the marker on the surgical tool, determining the location of the surgical tool and mapping the tool model into the spatial model. In case a processor is used which is configured for all these steps, no external processor is required.

The viewing device 5 may also comprise an augmented reality device 8. This is used to superimpose images over the users view, for example using see-through glasses which project holograms in front of the user's eyes, or video-see through glasses where the video image of the real world is augmented with virtual images and where the result is presented to the user's eyes . . . It may be used to superimpose images of the tool model onto the location of the tool, or to superimpose other models in space, such as superimposing models based on scans of a patient onto the exact location of the scanned part of the patient. This is especially useful when combined with the superimposed image of the tool model, because the user can then see the exact location of the working part with respect to tissue, like an organ, it is submerged in.

Figure 5A:
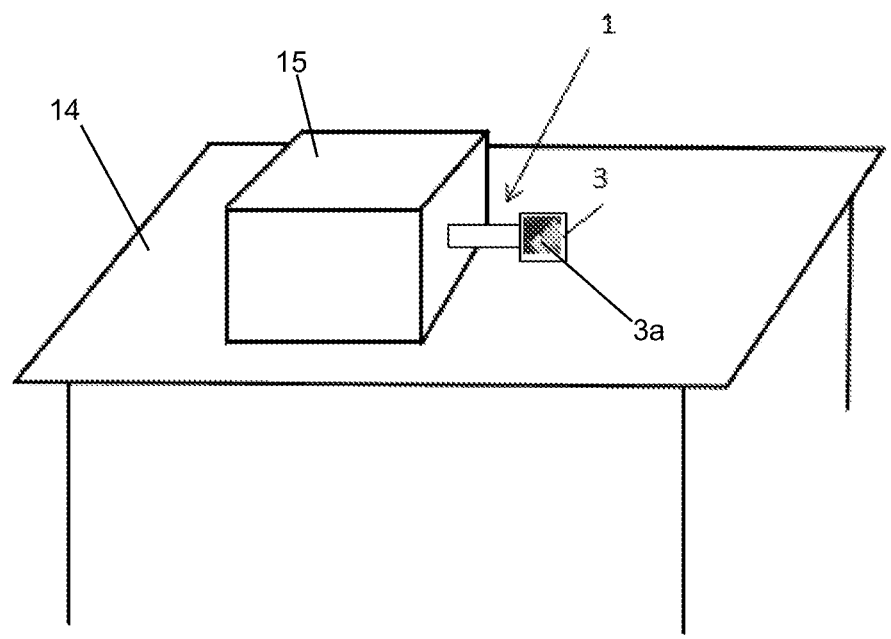
FIG. 5a shows the view of the camera.

FIG. 5 shows highly schematic three relevant views used in the method according to the invention. FIG. 5a shows the view seen and captured by the camera 6. It shows an environment (in this case, the table 14 and the cubic object 15 on it), and the surgical tool 1, with the marker 3 with visual image 3a clearly visible. The tool 1 is partly hidden, because the working part 2 is submerged in the cubic object and thus cannot be seen.

Figure 5B:
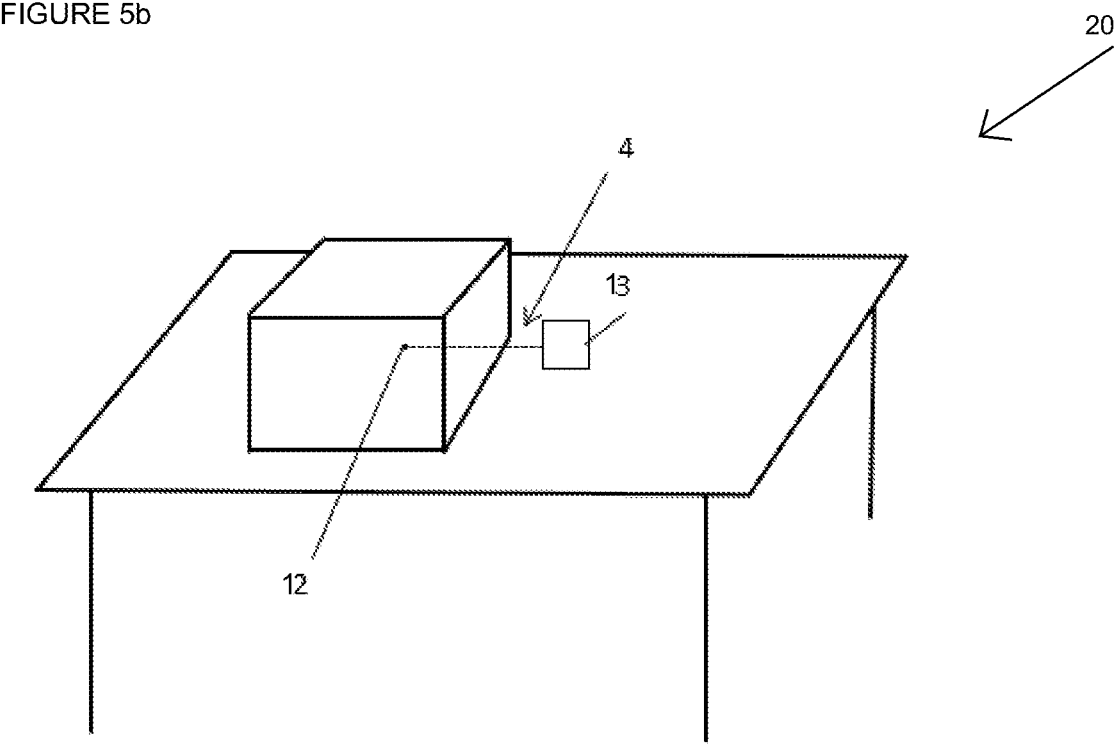
FIG. 5b shows the spatial model, and 5c shows the view of the camera or user.

FIG. 5b shows the spatial model 20 created based on the view of the camera. It shows the same environment as FIG. 5a. However, not the entire surgical tool is part of the spatial model, since it is a small and moving object that would normally not be incorporated. However, the software recognizes the marker 3, and uses this to make a mapping of the tool model 4 into the spatial model 20, which incorporates the location of the working part 12 of the tool model 4 in the spatial model.

Figure 5C:
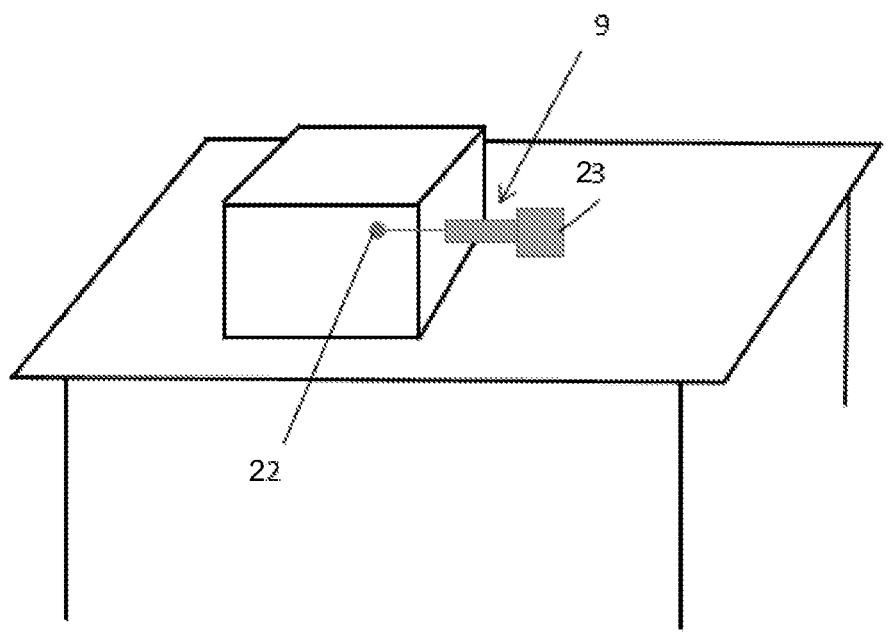
FIG. 5 shows the three views on the space in front of the camera used in the invention.

FIG. 5c then shows the view of the user if an augmented reality device is used to show a superimposed tool image 9 of the tool model 4 over the actual tool 1. This allows the user to see the location of the working part 22 of the tool image 9 within the item in which the surgical tool 1 is submerged.

FIG. 6 shows how additional models may be mapped into the spatial model, using a pointing element on the surgical tool 1. FIG. 6a shows an example of a body part of a patient, in this case the head. By touching the body part on several locations with the pointing element of the surgical tool 1, these locations are incorporated into the spatial model, as shown in FIG. 6b. This set of points in the spatial model can be used to determine where another model, such as a three dimensional scan of the brain, is to be projected. Using the points, the brain is projected in a correct position and rotation onto the head of the patient using augmented reality, so the user can see the exact layout, as seen in FIG. 6c.

In the below discussed FIGS. 6d, 6e, 7a, 7b and 7c, the view of a user wearing the viewing device is indicated by the rectangular border indicated in these figures.

Figure 6A:
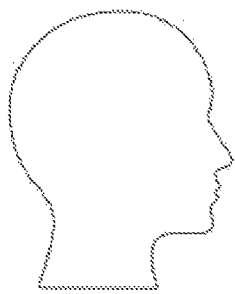
FIG. 6a shows an example of a patient.
Figure 6B:
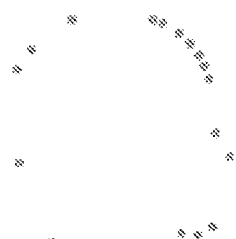
FIG. 6b shows the points that are indicated by the tool.
Figure 6C:
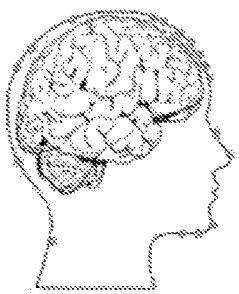
FIG. 6c shows the mapping of the model.
Figure 6D:
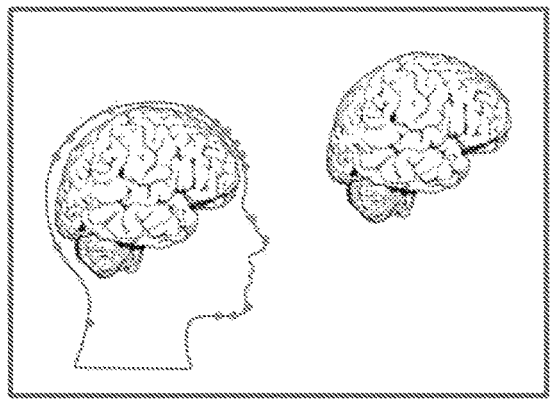
FIG. 6d shows the model mapped onto the object as well as mapped onto a location next to the object.
Figure 6E:
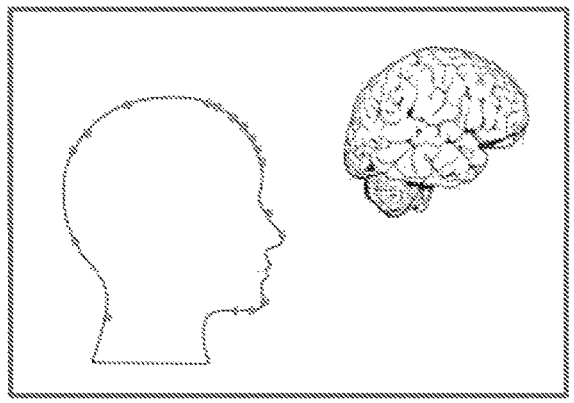
FIG. 6e shows the model mapped onto a location next to the object, whilst leaving the object itself not obscured by any mapping.

FIG. 6d shows that the model, such as the three dimensional scan of the brain, may be projected in the correct position and rotation onto the head of the patient and additionally in a position in the view shifted relative to the head of the patient. The user can then see the exact lay-out in the associated position relative to the patient, and in a position isolated from the view of the patient. FIG. 6e shows that it is also possible to only project the model of, in this case, the brain shifted relative to the head of the patient into the view. In FIGS. 6d and 6e the latter model is shown to be shifted to the right of the head of the patient in the view. It should be appreciated that this could be any other position shifted relative to the head of the patient. The shift of the model of, in this case, the brain could be effected by a linear mapping, such that the shifted model projected into the view is of a similar size as the model projected onto the head of the patient. This is shown in FIG. 6d. Alternatively, the mapping could be such that the shifted model projected into the view is smaller in size, or larger in size than the model that is or might be projected onto the head of the patient. In yet another option, the shifted model could be projected into the view such that it is in a rotated perspective from the model that is or might be projected onto the head of the patient.

Figure 7A:
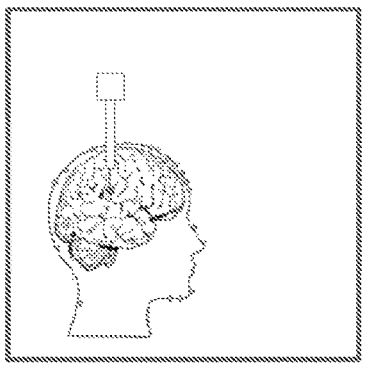
FIG. 7a shows a view similar to FIG. 6c, in which in addition also a visual tool image is mapped into the view.
Figure 7B:
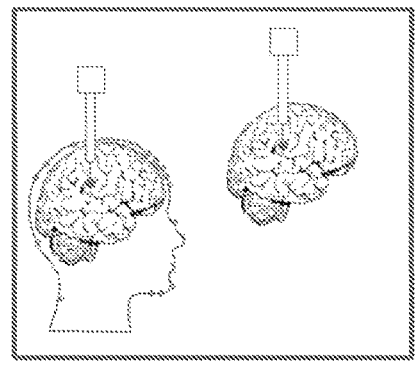
FIG. 7b shows a view similar to FIG. 6d, in which in addition also two visual tool images are mapped into the view.
Figure 7C:
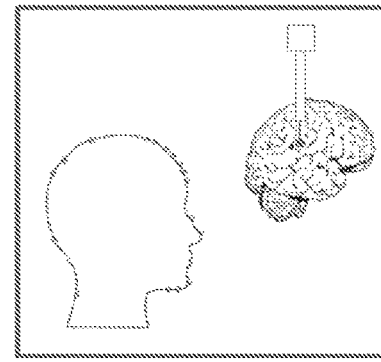
FIG. 7c shows a view similar to FIG. 6e, in which in addition also a visual tool image is mapped into the view.

FIGS. 7a-7c show how further additional models may be projected into the view, in this case a model of a surgical tool and a model of the three dimensional scan of the brain. Other combinations of additional models projected into the view not shown in FIGS. 7a-7c are conceivable. FIG. 7a shows an example, in which a three dimensional scan of the brain and a surgical tool are projected in a correct position and rotation onto the head of the patient using augmented reality. FIG. 7b shows an example, in which the three dimensional scan of the brain and a surgical tool are projected in a correct position and rotation onto the head of the patient, and additionally in a position in the view shifted relative to the head of the patient. FIG. 7c then shows an example, in which the three dimensional scan of the brain and a surgical tool are projected only in a position in the view shifted relative to the head of the patient.

Figure 8:
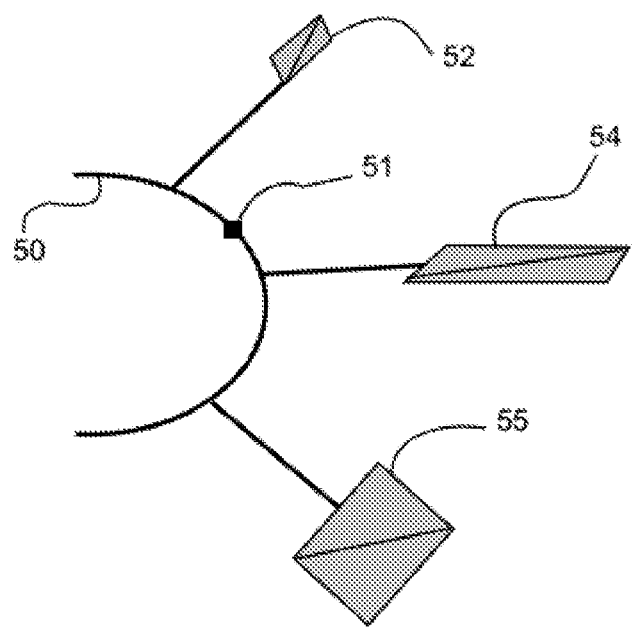
FIG. 8 shows schematically an example of marker frame or tool with a set of three frame markings respectively tool markings.

FIG. 8 shows schematically a marker frame 50 which in this example is configured to be fixed to the head of a patient. This marker frame 50 comprises a so called reference point 51. The marker frame is further provided with three frame markings 52, 54 and 55, which may each comprise a visual image. Each frame marking is the form of a visual image on a surface, such as a bitmap image. As shown each frame marking 52, 54 and 55 may be a similar shaped and sized body, each body being oriented differently with respect to the other bodies. The positions and orientation of each of these bodies are fixed relative to each other as well as relative to the reference point 51. The marker frame 50 shown in FIG. 8 may also be considered as a surgical tool, in which case the 'reference point' 51 will be the so called 'working part' of the tool.

As follows from the preceding, the invention can be used to visualize a complete 3D tool model with a holographic projector, smart glasses or any other AR device, even if it is partly submerged within the patients head or body. It can also be used to measure multiple points on a patients head or body, so that, with the aid of point-cloud-measuring techniques, a 3D model of anatomical structures can be accurately placed over a real or virtual patient. Both tool visualisation and anatomical structure visualisation are neuro-navigation techniques or in general medical navigation techniques.

The invention claimed is:

1. A method for the spatial mapping of a model of a surgical tool onto a spatial position of the surgical tool, comprising the following steps:

processor steps carried out by a processor unit,
providing a surgical tool having a working part and a marker in the form of a visual image on a surface, such as a bitmap image, the marker being arranged at a pre-determined marker location fixed relative to the working part of the surgical tool,
providing a tool model of the surgical tool, the tool model comprising at least the working part of the surgical tool and its location relative to the marker,
providing a viewing device configured to be carried by a user and comprising: a camera configured to capture:
a view of a user wearing the viewing device, and
the visual image when the visual image is within the view,
the camera generating camera data representative of the view captured by the camera,
bringing the surgical tool within the space viewed by the camera,
wherein the processor steps comprise:
creating, on the basis of the camera data, a spatial model of a space viewed by the camera,
identifying a representation of the marker in the camera data,
determining, on the basis of the camera data and the spatial model, a position and rotation of the representation of the marker with respect to the spatial model, and
creating a spatial mapping of the tool model in the spatial model, the creation of the spatial mapping being based on the tool model and the determined position and rotation of the marker;
wherein the processor steps further comprise:
generating, on the basis of the spatial mapping of the tool model in the spatial model, a visual tool image representing the surgical tool, and
wherein the method further comprises the step of:
superimposing the visual tool image in the view onto the surgical tool and/or onto a predetermined location shifted relative to the surgical tool,
wherein the visual tool image is projected into the view in its entirety whilst the surgical tool is within the view and partly hidden for the camera and/or user.

2. The method according to claim 1, further comprising the steps of:
moving the surgical tool to a multiple positions and/or rotations within the space viewed by the camera,
wherein the processor steps further comprise:
capturing a first set of camera data at each position and/or rotation,
creating, for each first set of camera data, a said spatial mapping of the tool model in the spatial model, and
obtaining a corrected spatial mapping of the tool model in the spatial model by processing the created spatial mappings with a calibration algorithm, such as an interpolation or artificial intelligence script.

3. The method according to claim 2, wherein the
visual tool image representing the surgical tool is generated on the basis of the corrected spatial mapping of the tool model in the spatial model.

4. The method according to claim 1, wherein the working part defines a pointed part, wherein the method further comprises the steps of:
providing, on the basis of a scan of an object, a visual 3-dimensional image of an object, the object having a multiple of reference points and the visual 3-dimensional image including per reference point an image point representative of the location of the associated reference point in the visual 3-dimensional image, touching with the pointed part the multiple of reference points on the object within the space viewed by the camera, capturing, at each touching of a reference point, a second set of camera data, wherein the processor steps further comprise:

determining for each reference point, on the basis of the tool model, the spatial model, and the associated second set of camera data, a spatial position representative of the position of the respective reference point within the spatial model; and wherein the method further comprises the step of:

projecting the visual 3-dimensional image into the view.

5. The method according to claim 4, wherein, in the step of projecting, the visual 3-dimensional image is projected into the view by superimposing each image point onto a predetermined location in the view, which predetermined location is shifted relative to the associated spatial position.

6. The method according to claim 4, wherein the reference points comprise mark points provided on the object.

7. The method according to claim 4, wherein the reference points comprise characteristic points of a contour of the object.

8. The method according to claim 7, wherein the characteristic points comprise predefined characteristic points.

9. The method according to claim 4, comprising a step of providing a marker frame to be attached to the object, which marker frame comprises a said reference point and is provided with a set of at least two frame markings, the frame markings of the set being arranged at mutually spaced, fixed positions on the frame and the said reference point being arranged at a predetermined reference point position fixed relative to the frame markings.

10. The method according to claim 9, wherein the set of frame markings comprises three frame markings.

11. The method according to claim 9, wherein each frame marking is in the form of a visual image on a surface, such as a bitmap image.

12. The method according to claim 1, wherein the visual marker comprises information about the shape and size of the surgical tool, and wherein, in the step of providing a tool model, the tool model is created on the basis of this information.

13. The method according to claim 12, wherein the tool image is generated on the basis of said information.

14. The method according to claim 1, wherein the visual image is no larger than 50 cm$^2$, such as no larger than 40 cm$^2$, preferably not smaller than 36 cm$^2$.

15. The method according to claim 1, wherein the marker of the surgical tool comprises a set of at least two tool markings, the tool markings of the set being arranged at mutually spaced, fixed positions on the surgical tool.

16. The method according to claim 15, wherein the set of tool markings comprises three tool markings.

17. The method according to claim 15, wherein each tool marking is in the form of a visual image on a surface, such as a bitmap image.

18. An assembly for creating a spatial mapping of a digital model of a surgical tool on a spatial position of a surgical tool, comprising:

a surgical tool having a working part and a marker in the form of a visual image on a surface, such as a bitmap image, the marker being arranged at a pre-determined marker location fixed relative to the working part of the surgical tool, a data carrier, configured to carry at least data of a digital tool model of the surgical tool, the tool model comprising at least the working part of the surgical tool and its location relative to the marker, a viewing device configured to be carried by a user and comprising:

a camera configured to:

capture a view of a user wearing the viewing device, capture the image when the image is within the view, and generate camera data representative of the view captured by the camera, and a processor unit, which is configured to carry out the processor steps of:

creating, on the basis of the camera data, a spatial model of a space viewed by the camera, identifying a representation of the marker in the camera data, determining, on the basis of the camera data and the spatial model, a position and rotation of the representation of the marker with respect to the spatial model, and creating a spatial mapping of the tool model in the spatial model, the creation of the spatial mapping being based on the tool model and the determined position and rotation of the marker;

generating, on the basis of the spatial mapping of the tool model in the spatial model, a visual tool image representing the surgical tool, wherein the viewing device further comprises a projector;

wherein the processor unit and projector are configured to superimpose the visual tool image in the view onto the surgical tool and/or onto a predetermined location shifted relative to the surgical tool, wherein the processor unit and projector are configured to project the visual tool image into the view in its entirety whilst the surgical tool is within the view and partly hidden for the camera and/or user.

* * * * *